United States Patent [19]

Kéri et al.

[11] Patent Number: 4,950,481

[45] Date of Patent: Aug. 21, 1990

[54] SKIN REGENERATING AND HYDRATING COSMETIC COMPOSITIONS AND PROCESS FOR THE PREPARATION OF THE ACTIVE INGREDIENT

[75] Inventors: Tibor Kéri; Jánosné Kristof, both of Debrecen, Hungary

[73] Assignee: Innofinance Altalanos Innovacios Penzintezet, Budapest, Hungary

[21] Appl. No.: 879,113

[22] PCT Filed: Sep. 20, 1985

[86] PCT No.: PCT/HU85/00057

§ 371 Date: May 7, 1986

§ 102(e) Date: May 7, 1986

[87] PCT Pub. No.: WO86/01713

PCT Pub. Date: Mar. 27, 1986

[30] Foreign Application Priority Data

Sep. 21, 1984 [HU] Hungary ............................ 3568/84

[51] Int. Cl.$^5$ ............................................. A61K 35/78
[52] U.S. Cl. .................................................. 424/195.1
[58] Field of Search ..................................... 424/195.1

[56] References Cited

U.S. PATENT DOCUMENTS 3,530,217 9/1970 White et al. ........................ 424/162

FOREIGN PATENT DOCUMENTS 2019525 1/1987 Japan .
856914 12/1960 United Kingdom .

OTHER PUBLICATIONS

Chem Abstracts 97:124,306b.
Chem. Abstracts 77:132,988p.
Chem. Abstracts 99:209,799f.
Chem. Abstracts 102:23,153r.
Chem. Abstracts 99:138,379f.
Chem. Abstracts 93:148,406c.
Chem. Abstracts 100:48,568b.
Chem. Abstracts 94:28,794p.
Chem. Abstracts 88:92,378k.
Chem. Abstracts 97:195,816d.

*Primary Examiner*—John W. Rollins
*Attorney, Agent, or Firm*—Herbert Dubno; Jonathan Myers

[57] ABSTRACT this invention is concerned with skin regenerating and hydrating cosmetic compositions which contain as active ingredient the extract of nodulous corn-stalk and-/or corn-hypsophyll and/or corn-cob and/or corn-silk.

8 Claims, No Drawings

SKIN REGENERATING AND HYDRATING COSMETIC COMPOSITIONS AND PROCESS FOR THE PREPARATION OF THE ACTIVE INGREDIENT

The invention relates to skin regenerating and hydrating cosmetic compositions and to a process for the preparation of the active ingredient.

BACKGROUND OF THE INVENTION

There are many excellent compositions on the cosmetic market, the greater part of which are based on synthetic elements. The skin regenerating compositions produced by the cosmetic factories improve the condition of the skin surface due to their fat and water content. Recently also the use of active ingredients of plant origin is discussed and cosmetic compositions containing herb extracts are on the market as well. The plant residues, which are obtained during the processing of agricultural cultivated plants and mainly as waste in the preserves industry, were not examined in view of the applicability in the cosmetic industry.

The object of the present invention was to obtain plant pieces possibly obtained as waste during the processing of agricultural cultivated plants, the extraction of which results in skin regenerating and hydrating active ingredient solutions.

The maize plant (Zea mays) was chosen for this aim. Maize is an industrial plant which came in Europe from America in 1493 and is known in Europe and now also in America mainly as a cultivated plant. It is cultivated to obtain grains, whereas the hypsophyll consisting of hard fibers, the corn-cob, corn-stalk and corn-silk (corn-beard) are discarded as usual waste.

Due to its mechanical effect the flour obtained from corn-cob has already been used in tooth pastes (HU-PS 118,580), for preparing small sticks for tooth polishing (DE-PS 656,808) and as adsorptive powders for drying exudates in the case of skin diseases caused by exudative dermatitis (U.S. Pat. Nos. 2,890,151 and 3,278,383). Corn-cob flour is also used for treating skin diseases of acne origin (U.S. Pat. No. 3,530,217). No data are, however, described in these patent specifications relating to skin regenerating or hydrating effect of aqueous or alcoholic solutions prepared from corn-cob, corn-cob flour is not used for this purpose. Hair lotion is prepared from the filament of the maize plant according to U.K. Patent No. 856,914; a composition against loss of hair may be prepared from the extract of Artemisia to which optionally also maize beard deception is added (U.K. Patent No. 2,060,378). The skin regenerating and hydrating effects of the maize beard were not, however, examined, and so a composition for this purpose was not produced.

BRIEF DESCRIPTION OF THE INVENTION

From our experiments it has been surprisingly found that by the extraction of the above mentioned pieces of the maize plant an active ingredient solution was obtained which was excellently suitable for calming inflamed skin, improving the scarfskin formation of wounded skin for light protecting, for treating pustules of other inflammatory formations when admixed in a suitable ratio with diluents and/or vehicles and optionally other known substances used in the cosmetic industry, e.g. propolis as disinfectant.

DETAILED DESCRIPTION OF THE INVENTION

The present invention relates to skin regenerating and hydrating cosmetic compositions comprising the extract of nodulous corn-stalk and/or corn hypsophyll and/or corn-cob and/or corn-silk (Zea mays) as active ingredient together with the usual vehicles and/or diluents.

The extract is prepared from the plant pieces with water or with a mixture of water and a water miscible organic solvent, preferably with the mixture of ethanol and water by steeping or boiling.

After filtering the extract the solution of the active ingredient is formulated directly or after lyophilization with the usual cosmetic vehicles and/or diluents.

The compositions of the invention show the expected favorable effect.

The face lotion (Example 9) was examined on 50 women aged from 20 to 63 years. The cream was applied after thorough cleaning twice a day, in the morning and the evening. The treatment was continued for two weeks. The following types of the face skin were examined: 40 slightly dry, 10 sensitive, dry skins. The cream has been absorbed well during each treatment, the skin became smooth, velvety. During the treatment no allergic reaction, irritative dermatitis or hypersensitiveness were observed.

The body lotion (Example 11) was tested on 22 women aged from 19 to 72 years. The composition was applied after thorough washing twice a day, in the morning and the evening. The treatment was continued for two weeks. The following types of skin were examined: 2 normal sensitive, 4 dry sensitive, 8 dry and 8 normal skins. The composition has been absorbed well during each treatment, the skin became velvety, smooth, the skin tightening and dryness, which occurred after washing (having a bath or shower-bath) stopped and the skin was calmed and refreshed. No allergic reaction, irritative dermatitis or hypersensitiveness were observed.

The following non-limiting Examples show the compositions of the invention and the preparation of the active ingredient.

EXAMPLE 1

Hypsophylls obtained from the harvested crop of the maize plant (1 kg), corn beard (0.1 kg), corn-cob deprived from the grains (1 kg) and nodulous corn-stalk (1 kg) were dried at 20° C. in a manner usual for the herbs, then crushed. 1 kg of the crushed substance was suspended in 3.75 l of water and steeped in a dry, cool place for 24 hours. After filtration the solution was boiled, then a 15% by vol. solution was prepared with cosmetic vaseline oil. The solution was stored in dry, cool, dark place until use.

EXAMPLE 2

Hypsophylls obtained from harvested crop were dried as in Example 1 and after crushing 4.25 l of deionized water were added to 1 kg of the crushed substance. The mixture was boiled for 2 hours, the resulting solution was filtered, then diluted with deionized water to its tenfold volume and closed hermetically until use. It was stored in a dry, cool, dark place.

EXAMPLE 3

Hypsophylls obtained from the crop of ripe maize plant and corn-cob separated from the grains were dried as in Example 1, then crushed. 1 kg of the crushed substance was steeped in 4.00 l to 70% aqueous alcohol, then the solution was filtered and after having been covered it was stored in dry, cool, dark place.

EXAMPLE 4

Hypsophylls obtained from the crop of ripe maize plant, the nodulous corn-stalk and the corn-silk were ground, 1 kg of the ground substance was suspended in 5 l of deionized water and steeped in a dry, cool place for 36 hours. After filtration the solution was boiled and closed hermetically then stored in a dry, cool, dark place until use.

EXAMPLE 5

Hypsophylls obtained from the crop of ripe maize plant were dried as in Example 1, then pulverized. 1 kg of the pulverized substance was steeped in 1.5 l of 70% aqueous alcohol at ambient temperature for 96 hours. The solution was filtered and after having been covered it was stored in dry, cool, dark plane until use.

EXAMPLE 6

Hypsophylls obtained from the crop of ripe maize plant and corn-silk were dried as in Example 1, then after having been ground 1 kg of the ground substance was steeped in 4.00 l of 70% aqueous alcohol for 70 hours under continuous stirring. The solution was filtered and after having been covered it was stored in a dry, cool, dark place.

EXAMPLE 7

Hypsophylls obtained from harvested crop of maize plant (1 kg), corn-silk (0.1 kg), corn-cob separated from the grains (0.05 kg) and the nodulous corn-stalk (0.5 kg) were dried as in Example 1 and crushed. 1 kg of the crushed substance was suspended in a 3.5 l of water and steeped in cool place for 24 hours. After filtration the solution was freeze dried (lyophilized) then after having been closed hermetically it was stored until use.

EXAMPLE 8

| Skin regenerating and hydrating body lotion | |
|---|---|
| Components | % by weight |
| Extract of Example 7 | 18.00 |
| Cetyl alcohol | 1.83 |
| Stearin | 4.70 |
| Vaseline oil (cosmetic quality) | 2.33 |
| Castor oil | 1.83 |
| Sodium laurylsulfate | 1.17 |
| Sorbitol | 3.60 |
| Glycerol | 6.00 |
| Nipagine | 0.20 |
| Tocopherol acetate | 0.05 |
| Perfume oil | 0.10 |
| Deionized water | 60.19 |

EXAMPLE 9

| Skin regenerating and hydrating face lotion | |
|---|---|
| Components | % by weight |
| Extract of Example 7 | 18.00 |
| Cetyl alcohol | 1.50 |

-continued

| Skin regenerating and hydrating face lotion | |
|---|---|
| Components | % by weight |
| Stearin | 4.50 |
| Vaseline oil (cosmetic quality) | 2.50 |
| Castor oil | 0.80 |
| Vaseline MD | 2.00 |
| Sodium laurylsulfate | 1.17 |
| Sorbitol | 3.70 |
| Glycerol | 6.00 |
| Nipagine | 0.20 |
| Tocopherol acetate | 0.05 |
| Perfume oil | 0.10 |
| Deionized water | 59.48 |

EXAMPLE 10

| Skin regenerating composition for hand treatment | |
|---|---|
| Components | % by weight |
| Extract of Example 7 | 18.00 |
| Cetyl alcohol | 6.40 |
| Stearin | 2.80 |
| Vaseline MD | 2.80 |
| Vaseline oil (cosmetic quality) | 2.80 |
| Castor oil | 0.30 |
| Glycerol monostearate | 0.50 |
| Lanoline | 3.00 |
| Sodium laurylsulfate | 0.83 |
| Sorbitol | 3.00 |
| Glycerol | 4.73 |
| Propylene glycol | 2.00 |
| Nipagine | 0.20 |
| Tocopherol acetate | 0.07 |
| Vitamin A | 0.01 |
| Vitamin K-III | 0.05 |
| Perfume oil | 0.13 |
| Propolis | 0.11 |
| Deionized water | 52.27 |

EXAMPLE 11

Skin regenerating and hydrating body lotion

The composition is the same as that of Example 8, wherein the 18.00% by weight extract of the active ingredient can be prepared according to any of Example 1 to 6.

EXAMPLE 12

| Skin regenerating and hydrating lotion for shower-bath | |
|---|---|
| Components | % by weight |
| Hostapur SAS (Hoechst AG.) | 20.00 |
| Genapol AMS (Hoechst AG.) | 40.0 |
| Betain | 10.0 |
| Genapol PMS (Hoechst AG.) | 2.0 |
| Maize oil | 2.0 |
| Extract of Example 2 | 20.0 |
| Perfume substance | 0.6 |
| Deionized water | 5.4 |

EXAMPLE 13

| Skin regenerating and hydrating tonic | |
|---|---|
| Components | % by weight |
| Extract of Example 5 | 28.00 |
| Retinoin acid | 0.05 |
| Ethanol (96%) | 61.25 |
| Propylene glcol | 10.00 |
| Tween 20 | 0.50 |

-continued

| Skin regenerating and hydrating tonic | |
|---|---|
| Components | % by weight |
| Perfume substance | 0.20 |

EXAMPLE 14

| Skin regenerating and hydrating liquid soap | |
|---|---|
| Components | % by weight |
| Extract of Example 7 | 3.7 |
| Genapol T (Hoechst AG.) | 3.0 |
| Genapol LRO (Hoechst AG.) | 33.3 |
| Medilan KA (Hoechst AG.) | 8.0 |
| Sodium chloride | 1.3 |
| Distilled water | 50.5 |
| Perfume substance | 0.2 |

EXAMPLE 15

| Skin regenerating and hydrating face cleansing emulsion | |
|---|---|
| Components | % by weight |
| Extract of Example 1 | 35.0 |
| Hostaphat KL 340N (Hoechst AG.) | 2.0 |
| Hostacerin DGS (Hoechst AG.) | 4.0 |
| Hostacerin PN 73 (Hoechst AG.) | 0.6 |
| Paraffine oil | 5.0 |
| Isopropyl palmitate | 6.0 |
| Propylene glycol | 3.0 |
| Distilled water | 44.2 |
| Perfume substance | 0.2 |

What is claimed is:

1. A skin-regenerating and hydrating composition which consists essentially of an aqueous or a water-miscible organic extract of maize waste pieces selected from the group consisting of nodulus cornstalk, corn hypsophyll, corncob and mixtures thereof as active ingredient together with a cosmetically acceptable vehicle or diluent.

2. The skin-regenerating and hydrating composition defined in claim 1 wherein the aqueous or water-miscible organic extract of maize waste pieces consists of nodulus cornstalk.

3. The skin-regenerating and hydrating composition defined in claim 1 wherein the aqueous or water-miscible organic extract of maize waste pieces consists of corn hypsophyll.

4. The skin-regenerating and hydrating composition defined in claim 1 wherein the aqueous or water-miscible organic extract of maize waste pieces, further includes an aqueous or water-miscible organic extract of corn silk.

5. A method of treatment to calm inflamed skin or to improve scarfskin formation of wounded skin for light protection, which comprises the step of applying to the skin a cosmetically effective amount of a skin-regenerating and hydrating composition which consists essentially of an aqueous or water-miscible organic extract of maize waste pieces selected from the group consisting of nodulus corn-stalk, corn hypsophyll, corncob, and mixtures thereof as active ingredient together with a cosmetically acceptable vehicle or diluent.

6. The method of treatment defined in claim 5 wherein the aqueous or water-miscible organic extract of maize waste pieces consists of nodulus cornstalk.

7. The method of treatment defined in claim 5 wherein the aqueous or water-miscible organic extract of maize waste pieces consists of corn hypsophyll.

8. The method of treatment defined in claim 5 wherein the aqueous or water-miscible organic extract of maize waste pieces, further includes an aqueous or water-miscible organic extract of corn silk.

* * * * *